United States Patent [19]

Brown et al.

[11] Patent Number: 5,427,912

[45] Date of Patent: Jun. 27, 1995

[54] ELECTROCHEMICAL ENZYMATIC COMPLEMENTATION IMMUNOASSAY

[75] Inventors: Mary E. Brown, Indianapolis; Lance S. Kuhn, Fishers; Robert J. McEnroe, Noblesville; Rebecca W. Muddiman, Indianapolis; Mary L. Ochs, Fishers, all of Ind.

[73] Assignees: Boehringer Mannheim Corporation, Indianapolis, Ind.; Boehringer Mannheim GmbH, Mannheim, Germany

[21] Appl. No.: 113,548
[22] Filed: Aug. 27, 1993
[51] Int. Cl.⁶ .................................. G01N 33/535
[52] U.S. Cl. ........................... 435/7.6; 435/18; 435/817; 435/968; 204/403
[58] Field of Search ............. 435/7.6, 18, 817, 968; 204/403

[56] References Cited

U.S. PATENT DOCUMENTS

| | | | |
|---|---|---|---|
| 4,378,428 | 3/1983 | Farina et al. | 435/7 |
| 4,708,929 | 11/1987 | Henderson et al. | 435/7 |
| 4,785,080 | 11/1988 | Farina et al. | 530/402 |
| 4,830,959 | 5/1989 | McNeil et al. | 435/7 |
| 4,912,041 | 3/1990 | Batchelor et al. | 435/101 |
| 4,950,612 | 8/1990 | Khanna et al. | 436/505 |
| 4,956,274 | 9/1990 | Khanna et al. | 435/7 |
| 4,963,245 | 10/1990 | Weetail | 204/403 |
| 5,032,503 | 7/1991 | Khanna et al. | 435/7.6 |
| 5,037,735 | 8/1991 | Khanna et al. | 435/7.6 |
| 5,106,950 | 4/1992 | Farina et al. | 530/345 |
| 5,120,653 | 6/1992 | Henderson | 435/252.33 |
| 5,124,253 | 6/1992 | Foulds et al. | 435/21 |
| 5,212,081 | 5/1993 | Coty et al. | 435/188 |
| 5,229,282 | 7/1993 | Yoshioka et al. | 435/177 |

FOREIGN PATENT DOCUMENTS

| | | |
|---|---|---|
| 0125139 | 11/1984 | European Pat. Off. |
| 0150999 | 8/1985 | European Pat. Off. |
| 0328380 | 8/1989 | European Pat. Off. |
| 0546536 | 6/1993 | European Pat. Off. |
| WO8603837 | 7/1986 | WIPO |
| WO8604926 | 8/1986 | WIPO |
| WO9013569 | 11/1990 | WIPO |
| 2991/16630 | 10/1991 | WIPO |

OTHER PUBLICATIONS

Y. Xu et al., Heterogeneous Enzyme Immunoassay of Alpha-Fetoprotein in Material Serum by Flow-injection Amperiometric Detection of 4-Aminophenol, (1990) 1941-1944, Clin. Chem. 36/11.

Thompson et al., Comparison of Methods for Following Alkaline Phosphatase Catalysis: Spectrophotometric versus Amperometric Detection, (1991) 90-95, Analytical Biochemistry 192.

Gil et al., Competitive Heterogeneous Enzyme Immunoassay for Theophyline by Flow-injection Analysis with Electrochemical Detection of p-Aminophenol, (1990) 662-665, Clin. Chem. 36/4.

Jenkins et al., The Use of Ion Pairing Reagents to Reduce Non-specific Adsorption in a Solid Phase Electrochemical Enzyme Immunoassay, (1990) 99-104, Contributed Article vol. 13 No. 2.

Wright et al., Sequestration Electrochemistry: The Interaction of Chlorpromazine and Human Orosomucoid, (1988) 290-293 Analytical Biochemistry 171.

Jenkens et al., Extending the Detection Limit of Solid—Phase Electrochemical Enzyme Immunoassay to the Attomole Level (1988) 292-299 Analytical Biochemistry 168.

*Primary Examiner*—David Saunders
*Attorney, Agent, or Firm*—D. Michael Young; Max J. Kenemore; Marilyn L. Amick

[57] ABSTRACT

An immunoassay diagnostic kit, method, and apparatus for electrochemically determining the concentration of an analyte in a sample. A mixture is formed which includes the sample, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme hydrolyzes the labeled substrate, resulting in the generation of an electroactive label, which can then be oxidized at the surface of an electrode. A current resulting from the oxidation of the electroactive compound can be measured and correlated to the concentration of the analyte in the sample.

54 Claims, 5 Drawing Sheets

(Prior art)

ELECTROCHEMICAL ENZYMATIC COMPLEMENTATION IMMUNOASSAY

FIELD OF THE INVENTION

This invention relates generally to the field of electrochemical immunoassay.

BACKGROUND OF THE INVENTION

Radioimmunoassay was developed in 1960 by Yarlow and Berson as a method for detecting or quantitating antigens or antibodies using radiolabeled reactants. Since the initial studies in 1960, radioimmunoassay (RIA) has developed into a versatile analytical technique, particularly useful in clinical laboratories to quantitate a wide variety of compounds. With RIA, the unknown concentration of an unlabeled antigen is determined by comparing its inhibitory effect on the binding of a radioactively-labeled antigen to an antibody. RIAs do have a number of significant limitations, however, including a limited shelf-life, high cost, and potential environmental harm.

The disadvantages associated with RIAs led to the development of the enzyme immunoassay (EIA), in which the activity of an enzyme is measured to quantitate an analyte. EIAs are subdivided into heterogeneous assays and homogeneous assays. Heterogeneous EIAs require a physical separation of the antibody-bound, labeled analyte from the unbound labeled analyte. With homogeneous EIAs, a separation step is not required. Homogeneous EIAs have been successful commercially because of their speed, simplicity, and automation. The enzymatic activity associated with EIAs is often monitored spectrophotometrically, using a substrate which produces a unique chromophore as a result of an enzymatic reaction.

In addition to using spectrophotometric detection techniques, EIAs have been developed which use electrochemistry to monitor activity of the enzyme label. With electrochemical detection, the active enzyme causes the formation of an active electron mediator or a redox couple from an inactive substrate. The activated mediator or redox couple then shuttles electrons from the enzyme to the electrode or from the electrode to the enzyme. The resulting current can be measured and correlated to analyte level.

Direct electrochemical enzymatic assays (nonimmunological) are also known in which the presence or absence of the analyte to be measured causes an electroactive compound to be cleaved from a non-electroactive substrate. The electroactive compound may then be oxidized or reduced and the resulting current measured.

Enzyme complementation immunoassays have been developed, such as CEDIA ® (Cloned Enzyme Donor ImmunoAssay—a registered trademark of the Microgenics Corporation) technology, an example of which is described by Henderson, U.S. Pat. No. 4,708,929, issued Nov. 24, 1987, which is hereby incorporated by reference. CEDIA ® technology involves the use of enzyme-acceptor and enzyme-donor polypeptides prepared by recombinant DNA techniques or chemical polypeptide synthesis techniques which are capable of combining spontaneously in solution to form an active enzyme complex. The enzyme-donor polypeptide is linked to an analog of the analyte to be measured (enzyme-donor polypeptide conjugate). The presence of antibody bound to the enzyme-donor polypeptide conjugate prevents the spontaneous reassembly of the enzyme subunits. When analyte in a sample is introduced, the sample analyte competes with the enzyme-donor polypeptide conjugate for antibody, resulting in increasing enzymatic activity with increasing amounts of sample analyte. The amount of enzymatic activity is then monitored spectrophotometrically.

SUMMARY OF THE INVENTION

This invention is based on the novel combination of CEDIA ® technology (enzymatic complementation immunoassay) with electrochemical detection of enzymatic activity in order to determine the concentration of an analyte in a fluid sample. The advantages that result from this combination include the speed and simplicity of a homogeneous EIA, enhanced analyte sensitivity, a much smaller sample volume requirement, and the adaptability of the assay to a wide range of analytes. The assay components include an enzyme-acceptor polypeptide ("EA"), an enzyme-donor polypeptide linked to an analyte analog (enzyme-donor polypeptide conjugate - ("ED"), a substrate for enzymatic reaction, a label which is bound to the substrate and which is preferably nonelectroactive until cleaved from the substrate, and an antibody specific for the analyte to be measured.

The fluid sample containing the analyte is mixed with a first reagent (EA reagent) which includes EA and antibody. This mixture is then mixed with a second reagent (ED reagent) which includes ED and the labeled substrate. When EA and ED are present alone in an aqueous medium, complementation occurs, resulting in an active enzyme complex. However, in the presence of the sample analyte and antibody, ED and the sample analyte competitively bind to the antibody. When ED becomes bound to the antibody, it is unavailable for complementation with EA to form active enzyme. As a result, as the amount of analyte in the sample increases, less ED becomes bound to the antibody and more active enzyme is formed. The active enzyme then cleaves the label from the substrate. The label becomes electroactive at the measurement potential when it is cleaved and may be oxidized at the surface of an electrode. The current measured from the oxidation of the label may be correlated to the concentration of the analyte in the sample.

DETAILED DESCRIPTION OF THE INVENTION

Figure 1:
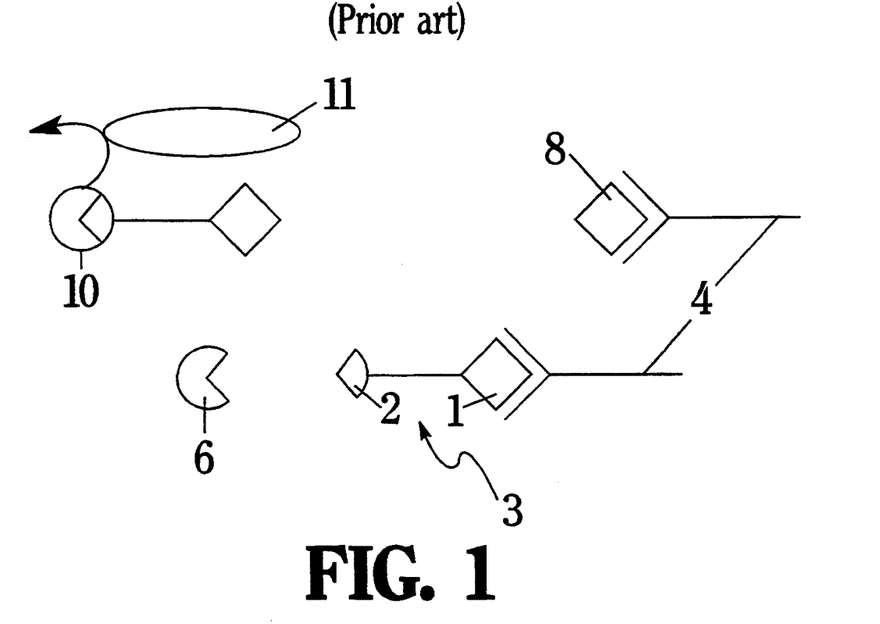
FIG. 1 is a block diagram of the primary CEDIA ® assay components and their interaction.

In one embodiment of CEDIA ® technology, inactive subunits of the β-galactosidase enzyme combine spontaneously in solution to form an enzyme that exhibits full β-galactosidase enzymatic activity. Referring to FIG. 1, analyte analog 1 is covalently attached to enzyme-donor polypeptide 2 to form enzyme-donor polypeptide conjugate 3 (ED). Analyte-specific antibody 4 can be used to inhibit reassembly of ED 3 with enzyme-acceptor polypeptide 6 (EA). When a sample containing analyte 8 is introduced, analyte 8 and ED 3 compete for binding to antibody 4. As the amount of analyte 8 increases, less ED 3 binds to antibody 4 and more active enzyme 10 is formed. Active enzyme 10 hydrolyzes enzyme substrate 11 (e.g., chlorophenol-red-β-D-galactopyranose (CPRG)), which then undergoes a color change and is monitored spectrophotometrically.

The Theophylline System Pack (a CEDIA ® assay, commercially available from Boehringer Mannheim Corporation, Cat. No. 1299883) is an EIA for the quantitative determination of theophylline in serum or plasma. The Theophylline System Pack was modified and optimized to allow measurements to be performed in accordance with the present invention. The contents of the Theophylline System Pack referred to above will now be described.

The enzyme used in the Theophylline System Pack is split into two inactive fragments, EA and ED, through the use of recombinant DNA technology. EA is a relatively large polypeptide containing approximately 95% of the native β-galactosidase enzyme protein sequence. ED is a small polypeptide containing approximately 5% of the native β-galactosidase enzyme. EA can spontaneously recombine with ED to form a catalytically active enzyme. The analyte analog is covalently bound to ED in a way that does not interfere with reassociation of the enzyme fragments.

The Theophylline System Pack includes four primary components: (i) EA reagent (lyophilize d), (ii) EA reconstitution buffer, (iii) ED reagent (lyophilize d), and (iv) ED reconstitution buffer. The EA reagent (lyophilized) includes the EA fragment of the enzyme, monoclonal anti-theophylline antibody, buffer salts, surfactants, carrier proteins, and preservative. A vial of the EA reagent is reconstituted with 20 ml (milliliters) of EA reconstitution buffer. The EA reconstitution buffer includes 3-(N-morpholino)propanesulfonic acid buffer solution (MOPS), stabilizers, and preservative.

The ED reagent (lyophilized) includes the ED fragment of the enzyme, buffer, chlorophenol-red-β-D-galactopyranoside (CPRG), surfactants, stabilizer, secondary antibody, and preservative. A vial of the ED reagent is reconstituted with 16 ml of ED reconstitution buffer, which is similar in composition to the EA reconstitution buffer.

Figure 2:
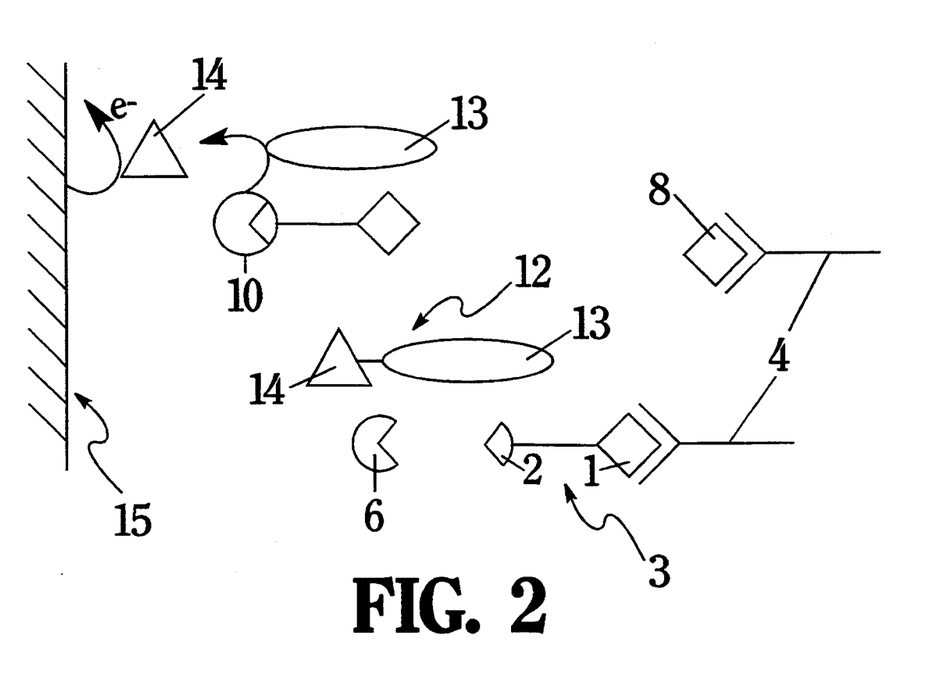
FIG. 2 is a block diagram of the primary components of the present invention and their interaction.

The Theophylline System Pack described above may be modified for use in the present invention. Referring to FIG. 2, analyte analog 1, enzyme-donor polypeptide 2, ED 3, antibody 4, EA 6, sample analyte 8, and active enzyme 10 all have the same function as in the CE-DIA ® assay described in FIG. 1. However, labeled substrate 12 is made by covalently linking label 14 to substrate 13 in such a way that label 14 is nonelectroactive at the measurement potential until cleaved from substrate 13 by enzymatic hydrolysis. Label 14 may then be oxidized at the surface of electrode 15 to produce a current which may be correlated to the detection or measurement of analyte 8 present in the sample being analyzed. The present invention allows an assay to be performed on a sample of about 25 μl (microliters), whereas the Theophylline System Pack assay requires a sample volume of about 250 μl.

The Theophylline System Pack was modified as described in tables 1 through 4, which identify the components, concentrations, and functions of the components in accordance with the present invention.

TABLE 1

Theophylline System Pack modifications - ED reagent

| Modified ED Reagent | Concentration | Function |
| --- | --- | --- |
| Potassium Phosphate, dibasic | 80.000 mM | buffer |
| Fragmented Bovine Serum Albumin (BSA) | 2.000 mg (milligrams)/ml | protects viability of antibody and enzymes |
| Heat inactivated goat anti-mouse serum (GAMS) | 47.600 ml/l (liter) | provides steric hindrance to antibody |
| Labeled substrate (see below) | | provides means for monitoring enzyme activity |
| ED-theophylline conjugate | 1.613 ml/l | enzyme donor fragment - coupled to theophylline |

TABLE 2

Theophylline System Pack modifications - ED reconstitution buffer

| Modified ED Reconstitution Buffer | Concentration | Function |
| --- | --- | --- |
| Potassium Phosphate, dibasic | 0.0205M (molar) | buffer |
| Potassium Phosphate, monobasic | 0.0295M | buffer |
| Sodium Chloride (NaCl) | 1.00M | prevents salting out of antibodies |
| Tween 20 (10% aqueous solution) | 0.020% by volume | surfactant |

TABLE 3

Theophylline System Pack modifications - EA reagent

| Modified EA Reagent | Concentration | Function |
| --- | --- | --- |
| Potassium Phosphate, dibasic | 4.000 mM (millimolar) | buffer |
| EA | 203.520 U (Units)/ml | enzyme acceptor fragment |
| Theophylline monoclonal antibody | 25 μg (micrograms)/ml | specific molecule against theophylline molecule |
| Theophylline high calibrator | 40 mg/l | shifts reaction into linear range of curve |

TABLE 4

Theophylline System Pack modifications - EA reconstitution buffer

| Modified EA Reconstitution Buffer | Concentration | Function |
| --- | --- | --- |
| Potassium Phosphate, dibasic | 0.0205M | buffer |
| Potassium Phosphate, monobasic | 0.0295M | buffer |
| Sodium Chloride (NaCl) | 1.00M | prevents salting out of antibodies |
| Magnesium Acetate | 0.0078M | provides source of $Mg^{2+}$ for |

-continued

| | | |
|---|---|---|
| Tween 20 (10% aqueous solution) | 0.020% | enzymatic reaction surfactant |

Reagent Preparation

The EA and ED reagents and reconstitution buffers described above were prepared as follows. EA reagent: a bulk potassium phosphate buffer with a concentration of 4.000 mM was prepared in deionized, distilled water. (Since an electrochemical measurement is being made in the present invention, it is important that the buffer is electrochemically inactive at the measurement potential.) The pH was adjusted to 7.1 at 25° C. by addition of 1N (normal) HCl (hydrochloric acid). The buffer was then filtered through sterile 0.2 μm (micrometer) cellulose acetate. The enzyme acceptor fragment (EA) was cut using sodium sulfate and the EA concentration was titered before it was added to the bulk buffer at about 200 U/ml (β-galactosidase units defined by its reaction with chlorophenol-red-β-D-galactopyranoside (CPRG), based on the extinction coefficient of the cleaved substrate). Theophylline monoclonal antibody was added to the reagent at a concentration of about, 25 μug/ml. Excess theophylline was then added to the reagent at a concentration of 40 mg/l. The excess theophylline increases the linearity of the system by shifting the low end of the calibration curve into the linear range. The reagent was then assayed versus a reference reagent and adjusted to achieve appropriate activity (a titration to ensure there is enough β-galactosidase, theophylline, and theophylline monoclonal antibody to measure the highest concentration of theophylline to be detected by the assay). The reagent was then filtered through a 0.2 μm cellulose acetate filter and 4 ml was lyophilized in a glass bottle.

ED reagent: a bulk potassium phosphate buffer with a concentration of 80.000 mM was prepared in deionized, distilled water. (As stated above, it is important that the buffer is electrochemically inactive at the measurement potential.) Pepsin-digested BSA was then added to the buffer at a concentration of 2.0 mg/ml. The addition of BSA (protein fragments) to the ED reagent reduces hydrolysis of the enzyme-donor polypeptide conjugate from proteases in the fluid sample (i.e., the BSA enhances stability of the antibody and ED—the resulting hydrophobic interactions maintain the conformation of proteins). The synthesis of pepsin-digested BSA is described by Coty et al. in example 2, column 7, lines 26–40 (using the 60 minute incubation period) of U.S. Pat. No. 5,212,081, issued May 18, 1993, which is hereby incorporated by reference. The pH was then adjusted to 7.1 at 25° C. Heat-inactivated goat anti-mouse serum (GAMS) was then added to achieve a protein concentration of 10 g (grams)/l. GAMS contains a second antibody, capable of binding to theophylline monoclonal antibody, that helps reduce background signal by providing extra steric hindrance to ensure the ED fragment does not complement with the EA fragment when ED is bound to the monoclonal theophylline antibody. A 120 mg/ml stock solution was made of an appropriate β-galactosidase labeled substrate (e.g., 4-(1,4,7,10-tetraoxadecyl)-1-naphthyl-β-D-galactopyranoside, 4methoxy-1-naphthyl-β-D-galactopyranoside or p-aminophenyl-β-D-galactopyranoside). Synthesis of these labeled substrates is described below. The labeled substrate stock solution was then added in sufficient amount to make sure enough labeled substrate was available for enzymatic hydrolysis at high analyte concentration. The reagent was then filtered through a 0.2 μm cellulose acetate filter. Finally, the enzyme-donor polypeptide conjugate (ED) was added. The reagent was then assayed versus a reference reagent, which contained the ED reagent components in known concentrations. 4 ml of the ED reagent was then lyophilized in a glass bottle.

EA reconstitution buffer: a potassium phosphate buffer was prepared at a concentration of 0.05M. Sodium chloride was added until the solution was 1.0M in sodium chloride, and magnesium acetate was added until its concentration was 0.0078M. A small amount of Tween 20 detergent (see table 4 above) was then added. The ED reconstitution buffer was prepared in the same manner, except that magnesium acetate was not added.

Preparation of enzyme-acceptor fragment EA and enzyme-donor polypeptide conjugate ED by recombinant DNA methods in accordance with the present invention is fully described in U.S. Pat. No. 4,708,929 (Henderson, issued Nov. 24, 1987), incorporated by reference above.

Substrates

Figure 3:
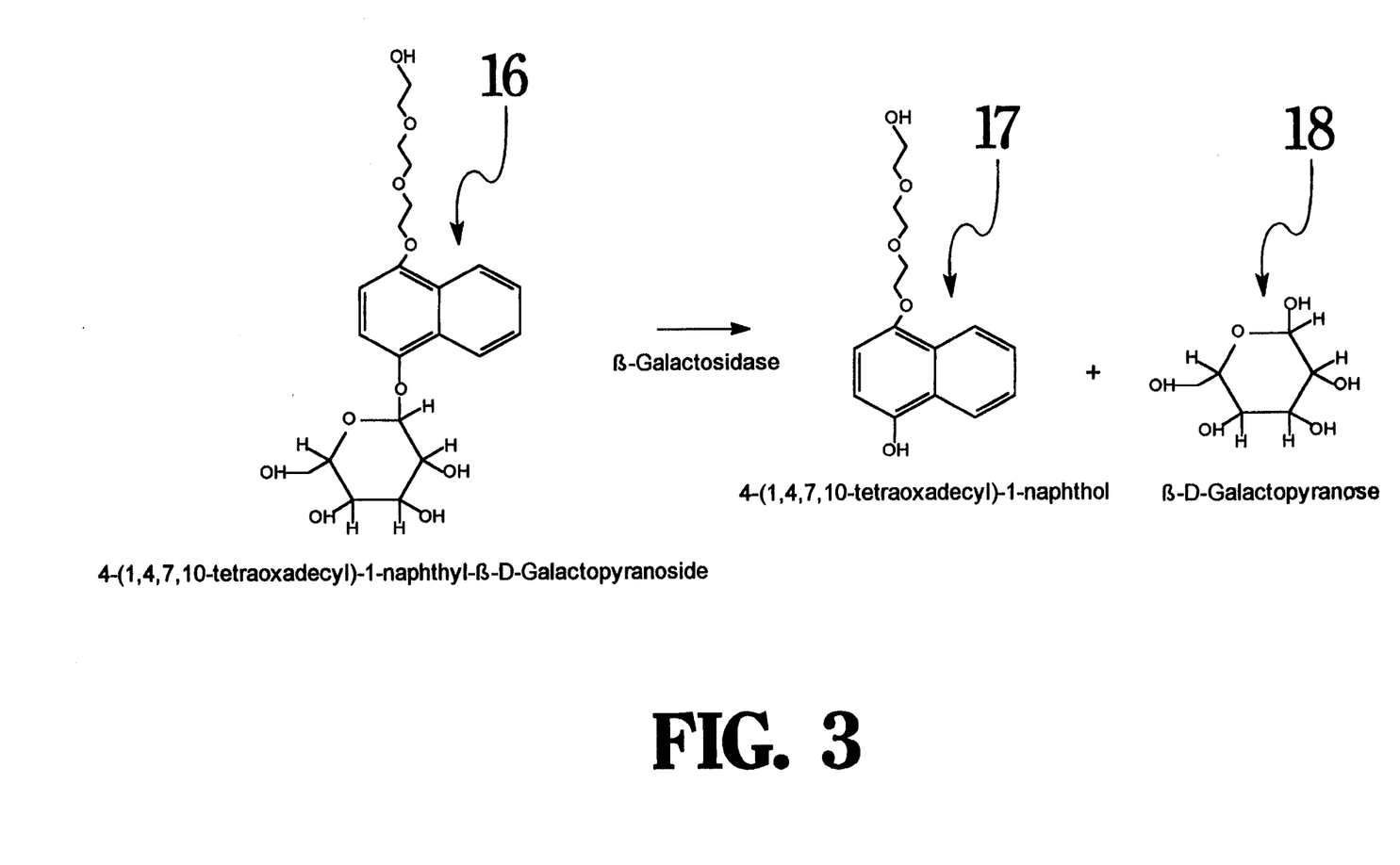
FIG. 3 is a representation of the biochemical events of the present invention, using the example of 4-(1,4,7,10-tetraoxadecyl)-1-naphthyl-$\beta$-D-galactopyranoside as a labeled substrate.

In the present invention, enzyme activity is monitored electrochemically by using an enzyme substrate which is covalently linked to a label. An example of such a labeled substrate is shown in FIG. 3. Labeled substrate 16 (4-(1,4,7,10-tetraoxadecyl)-1-naphthyl-β-D-galactopyranoside) is nonelectroactive until enzymatic hydrolysis cleaves electroactive label 17 (4-(1,4,7,10-tetraoxadecyl)-1-naphthol) from substrate 18 (β-D-galactopyranose). Label 17 (4-(1,4,7,10-tetraoxadecyl)-1-naphthol) is then oxidized at the surface of an electrode, resulting in a current which may be measured.

The β-galactosidase enzyme is especially suitable for use with the present invention. Use of this enzyme results in smaller background signals and therefore greater analyte sensitivity, since there is no natural β-galactosidase activity in human blood. β-galactosidase substrates that may be used with the present invention will now be described. (If enzymes other than β-galactosidase are used in the preparation of enzyme-acceptor fragment EA and enzyme-donor polypeptide conjugate ED, as described above, other substrates become necessary.)

In accordance with the present invention, the labeled substrate should be soluble in aqueous medium and is preferably electrochemically inactive when scanned in the potential range of $-0.6$ V (volts) to $+1.0$ V vs. Ag/AgCl. When cleaved from the substrate, the label should be electrochemically active in this same potential range. Preferences for the cleaved label include a near zero redox potential ($0.0V < E° < 0.5V$ vs. Ag/AgCl), electrochemical reversibility, and aqueous solubility. The substrate used in the Theophylline System Pack, CPRG, is not a preferable labeled substrate for the present invention because the label has a high oxidation potential and it is electrochemically irreversible.

Electrochemical characteristics of some β-galactosidase labeled substrates and their cleaved labels are provided in table 5.

TABLE 5

Examples of β-galactosidase labeled substrates and their cleaved labels

| Compound | Elec. Active | $E_{OX}$ vs. Ag/AgCl | Reversible | Solubility |
|---|---|---|---|---|
| resorufin-β-D-galactopyranoside | yes | −0.100 V | yes | soluble |
| resorufin (cleaved) | yes | −0.100 V | yes | soluble |
| 4-methoxy-1-naphthyl-β-D-galactopyranoside | yes | −0.10 V, +1.00 V | quasi, no | slightly |
| 4-methoxy-1-naphthol (cleaved) | yes | −0.10 V, +0.20 V | quasi, no | no |
| p-aminophenyl-β-D-galactopyranoside | no | — | — | soluble |
| p-aminophenol (cleaved) | yes | +0.18 V | yes | soluble |
| 4-(1,4,7,10-tetraoxadecyl)-1-naphthyl-β-D-galactopyranoside | yes | +0.05 V, +1.00 V | no, no | soluble |
| 4-(1,4,7,10-tetraoxadecyl)-1-naphthol (cleaved) | yes | +0.38 V | no | soluble |

Although it is preferable for the labeled substrate to be electrochemically inactive and the cleaved label electrochemically active, both may be electrochemically active so long as they are active at potentials at least 118 mV apart. (For example, labeled substrate 4-(1,4,7,10-tetraoxadecyl)-1-naphthyl-β-D-galactopyranoside is electrochemically active at +0.05 V and +1.00 V, but cleaved label 4-(1,4,7,10-tetraoxadecyl)-1-naphthol is only electroactive at +0.38 V.)

Referring to table 5, labeled substrate 4-(1,4,7,10-tetraoxadecyl)-1-naphthyl-β-D-galactopyranoside is the preferred labeled substrate for the present invention because of its aqueous solubility, which facilitates reagent formulation. Labeled substrates p-aminophenyl-β-D-galactopyranoside and 4-methoxy-1-naphthyl-β-D-galactopyranoside also work well but are not preferred since 4-methoxy-1-naphthyl-β-D-galactopyranoside is less soluble than 4-(1,4,7,10-tetraoxadecyl)-1-naphthyl-β-D-galactopyranoside and p-aminophenyl-β-D-galactopyranoside has slower kinetics (i.e., the label is released more slowly under conditions of enzymatic hydrolysis) than 4-(1,4,7,10-tetraoxadecyl)-1-naphthyl-β-D-galactopyranoside. Labeled substrate resorufin-β-D-galactopyranoside is an example of a β-galactosidase labeled substrate that does not work with the present invention, since it is electrochemically active at the measurement potential before and after cleavage.

Substrate Preparation

Synthesis of 4-(1,4,7,10-tetraoxadecyl)-1-naphthol (disclosed by Goeltner et al., Liebigs Ann. Chem., 1991, 1085–1089): 2.0 g (12.5 mmol) naphthohydroquinone is added to 80 ml triethylene glycol to yield 3.4 g (92%) of a violet oil which, after column chromatography (SO₂-saturated ethyl acetate), hardens into pink needles with a melting point of 70° C. The crude product, 4-(1,4,7,10-tetraoxadecyl)-1-naphthol, is then attached to β-D-galactopyranose to form labeled substrate 4-(1,4,7,10-tetraoxadecyl)-1-naphthyl-β-D-galactopyranoside as described below in the synthesis of 4-methoxy-1-naphthyl-β-D-galactopyranoside, except that 4-(1,4,7,10-tetraoxadecyl)-1-naphthol is used in place of 4-methoxy-1-naphthol.

Synthesis of 4-methoxy-1-naphthyl-62 -D-galactopyranoside (disclosed by Herrmann et al., U.S. Pat. No. 5,202,233, issued Apr. 13, 1993, which is hereby incorporated by reference): 96.1 g acetobromogalactose (1-bromo-2,3,4,6-tetra-O-acetyl-α-D-galactopyranose - from Fluka) is dissolved in 200 ml acetone and deoxygenated by passing in nitrogen. The solution is heated to boiling with continuous stirring and then there is added dropwise first a solution of 14.3 g potassium hydroxide in 13 ml water and subsequently a solution of 18.5 g 4-methoxy-1-naphthol in 200 ml acetone, in each case within the course of 10 minutes. During the addition, the reaction mixture should boil continuously under reflux. Subsequently, stirring is continued for 4 hours at the same temperature, then cooled, insolubles are filtered and the filtrate evaporated in a high vacuum. The remaining syrupy residue is digested three times with, in each case, 100 ml water and then used as crude product, without further purification, in the next synthesis step (below). To a suspension of 4-methoxy-1-naphthyl-2,3,4,6-tetra-o-acetyl-β-D-galactopyranoside in 150 ml anhydrous methanol is added, with the exclusion of moisture and within the course of 1 hour, 25 ml of a 0.5M sodium methanolate solution in anhydrous methanol so that the pH of the reaction mixture is kept at about 13. After conclusion of the reaction (TLC monitoring), the product is isolated by column chromatography on silica gel.

Methods of synthesis for p-aminophenyl-β-D-galactopyranoside and p-nitrophenyl-β-D-galactopyranoside and p-nitrophenyl-β-D-galactopyranoside are publicly known. Other commercially-available labeled substrates which could be used in accordance with the present invention include, but are not limited to, p-nitrophenyl-β-D-galactopyranoside, chlorophenol red-β-D-galactopyranoside (CPRG), o-nitrophenyl-β-D-galactopyranoside, umbelliferyl-β-D-galactopyranoside, o-methoxy-p-nitrophenyl-β-D-galactopyranoside, 3,4-dinitrophenyl-β-D-galactopyranoside, m-cyano-p-nitrophenyl-β-D-galactopyranoside, 4-nitrosalicylaldehyde-β-D-galactopyranoside, and 4-methyl-umbelliferyl-β-D-galactopyranoside.

Electrochemical Cell

Performing an assay in accordance with the present invention by using the aqueous reagents described above involves making an electrochemical measurement. One example of an electrochemical cell that can be used to make such an electrochemical measurement will now be described.

Figure 4:
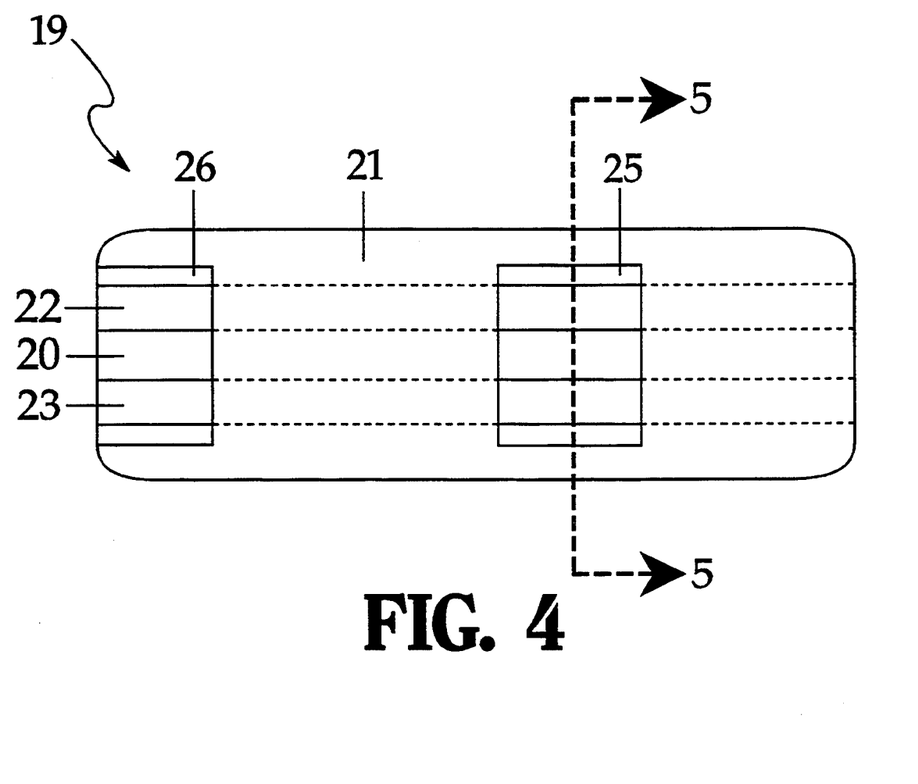
FIG. 4 is a schematic top view of an embodiment of an electrocell used with the present invention.
Figure 5:
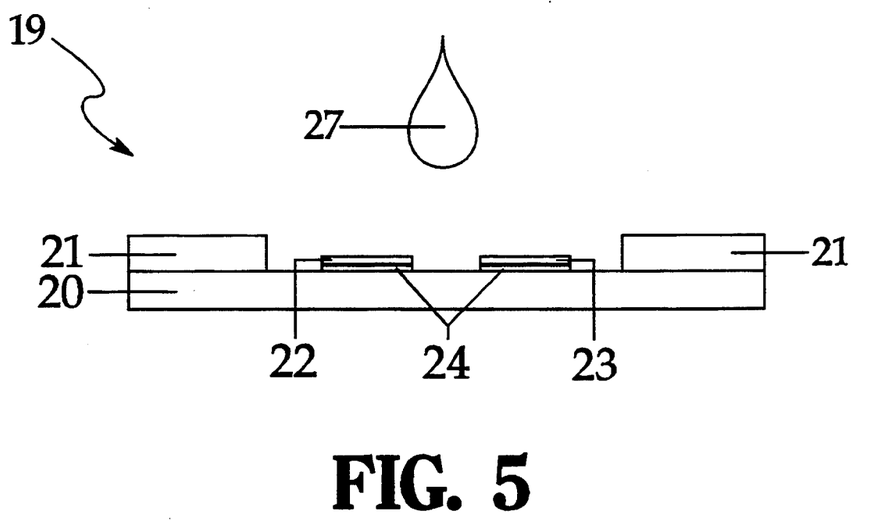
FIG. 5 is a schematic cross-sectional view of FIG. 4 taken along line 5—5 of FIG. 4.

Reference is now made to FIGS. 4 & 5. Electrocell (e-cell) 19 has a first insulating substrate 20, which is about 360 microns thick and made of polyester. Other substrates and thicknesses could also be used. Typically, plastics such as vinyl polymers and polyimides provide the electrical and structural properties which are desired. Working electrode 22 and counter electrode 23 are each about 0.1 micron thick, made of palladium, and are affixed to first insulating substrate 20 by the use of hot melt adhesive (not shown). In addition to palladium, other electrically conducting materials may be used for electrodes 22 and 23, including platinum, gold, silver, carbon, titanium, and copper. Noble metals are preferred because they provide a more constant, reproducible electrode surface area. Palladium is particularly preferred because it is one of the more difficult noble metals to oxidize. Silver is not preferred because it is more readily oxidized by air than the other noble metals listed above. Electrodes 22 and 23 should be sufficiently separated so that the electrochemical events at one electrode do not interfere with the electrochemical events at the other electrode.

Electrodes 22 and 23 are deposited on a backing of insulator material 24, a polyimide, to reduce the possibility of tearing the electrode before it is affixed to substrate 20. Backing 24 is about 25 microns thick. The electrode and polyimide combination is commercially available from Courtaulds Performance Films in California. Electrodes 22 and 23 extend from one end of substrate 20 to the other end in parallel configuration. The distance between electrodes 22 and 23 is about 1.2 mm (millimeters).

Second insulating substrate 21 is fixed on top of first insulating substrate 20 and electrodes 22 and 23 by the use of hot melt adhesive (not shown). Substrate 21 is about 250 microns thick, made of polyester, and includes sample window 25 which exposes substantially equal surface areas of electrodes 22 and 23. Sample window 25 is 4 mm by 6 mm and electrodes 22 and 23 are each 1.5 mm in width. Therefore, a surface area of about 6 mm$^2$ is exposed for each of the two electrodes. Substrate 21 also has cutout portion 26 at one end to allow an electrical connection between the electrodes and a power source (not shown) and a current measuring meter (not shown). As discussed above with substrate 20, other substrates and thicknesses may be used for substrate 21.

In the electrocell embodiment described above, the use of a working and a counter electrode are described. This embodiment has the advantage of being easy to manufacture. Although the described embodiment only has the reduced form of the label attached to the substrate, the oxidized form of the label (e.g., 4-(1,4,7,10-tetraoxadecyl)-1-naphthal) should also preferably be present in the reagent in high concentration (at least twice the concentration of the amount of the reduced form of the cleaved label (e.g., 4-(1,4,7,10-tetraoxadecyl)-1-naphthol) expected to be produced by the assay) when using the working/counter electrode design described above. Since the oxidation of the label is being measured, the oxidation and not the reduction should be the current-limiting event. Having an excess of the reduced form of the label helps ensure that the reduction of the label is not current-limiting.

Other two-electrode configurations are possible. For example, a two electrode electrocell using a reference electrode (e.g., Ag/AgCl) rather than a counter electrode or a three electrode electrocell using working, counter and reference electrodes are possible. The preferred embodiment of the referenced two or three electrode electrocells would not need the oxidized form of the label present in the reagent.

Example 1 theophylline assay using aqueous reagents

An assay for theophylline in accordance with the present invention and using the reagents made as described above was performed as follows. 20 ml of the EA reconstitution buffer was added to the lyophilized EA reagent and 16 ml of the ED reconstitution buffer was added to the lyophilized ED reagent. 293 $\mu$l (microliters) of the reconstituted EA reagent was dispensed into an incubated tube. 23 $\mu$l of a serum sample was then added to the reconstituted EA reagent and the solution was briefly and gently mixed. The reconstituted EA reagent/sample mixture was allowed to incubate at a temperature of 35°-37° C. for 4 minutes and 36 seconds. 220 $\mu$l of the reconstituted ED reagent was then added to the reconstituted EA reagent/sample mixture and the solution was briefly and gently mixed. The full mixture was then allowed to incubate at a temperature of 35°-37° C. for 19 minutes and 16 seconds.

After the final incubation, about 20 $\mu$l of the full mixture was applied to the sample window of the electrocell described above. The electrodes were electrically connected to a power source and a current measuring meter. A potential difference of 450 mV (millivolts) was applied between the two electrodes. Potential differences less than 450 mV can result in non-diffusion-limited currents. Potential differences greater than 450 mV can result in unneccesary oxidation of interfering compounds in the sample. The current generated was measured for about 5 seconds. The amount of current measured 3 seconds after application of the potential difference was then compared to a calibration curve and theophylline concentration in the serum sample was determined. Current reading times of less than 3 seconds result in less precise measurements, while current reading times greater than 3 seconds result in smaller currents and lower sensitivity. Minimal background signals were observed, since there is no $\beta$-galactosidase activity in human blood, the uncombined EA and ED fragments are not electrochemically active, and because there are few endogenous electrochemically active compounds in blood. As a result, practice of the present invention results in enhanced analyte sensitivity.

Example 2 theophylline assay using a dry-chemistry immunosensor

In addition to using the aqueous reagents and electrocell described above, the present invention could also be practiced by using a dry-chemistry immunosensor. Two examples of such an immunosensor will now be described.

Figure 6:
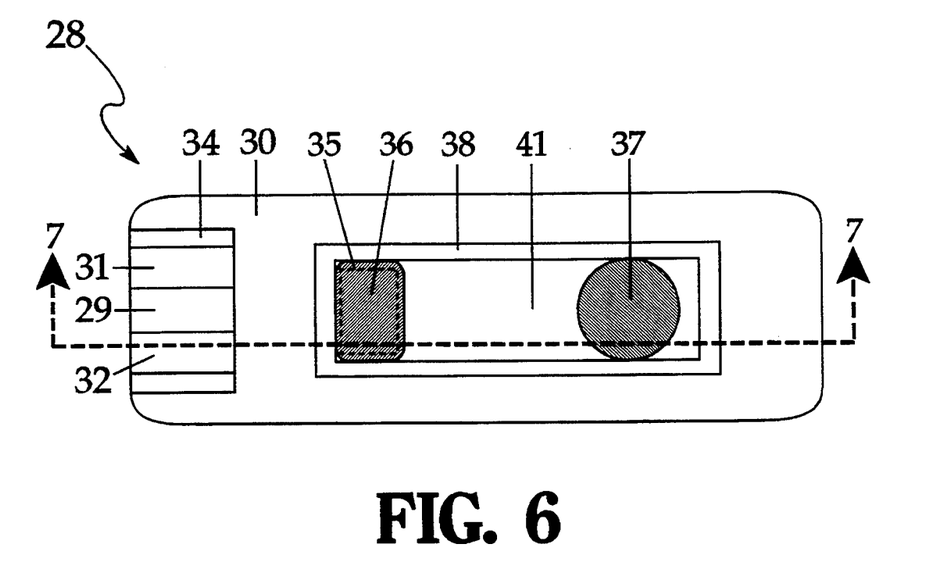
FIG. 6 is a schematic top view of an embodiment of an immunesensor of the present invention, excluding the fourth insulating substrate.
Figure 7:
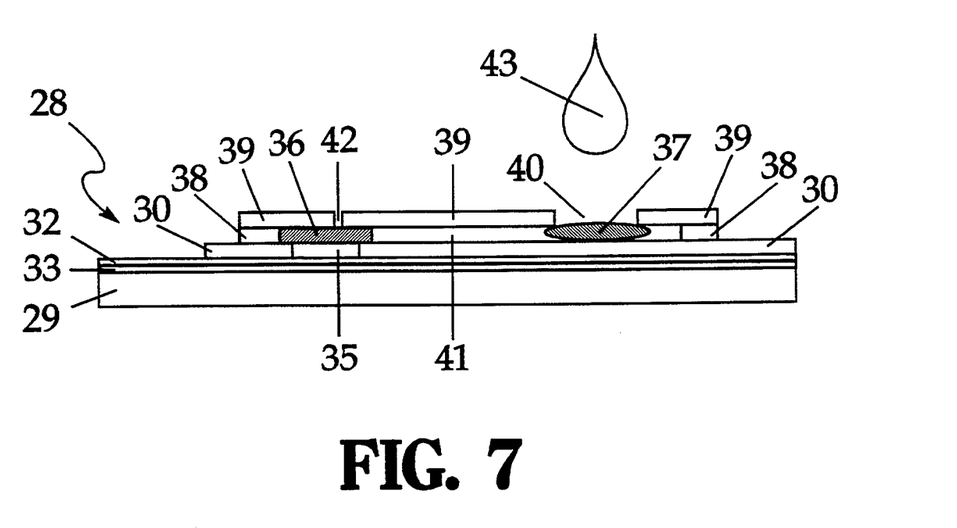
FIG. 7 is a schematic cross-sectional view of FIG. 6 taken along line 7—7 of FIG. 6, including the fourth insulating substrate.

Reference is now made to immunosensor 28 shown in FIGS. 6 & 7. First insulating substrate 29, working electrode 31, counter electrode 32, and insulator material 33 are all similar in composition and function to first insulating substrate 20, working electrode 22, counter electrode 23, and insulator material 24 described above in FIGS. 4 & 5. (A two-electrode electrocell and a three-electrode electrocell, utilizing working and reference electrodes, are also possible, as described above for electrocell 19.) Immunosensor 28 also has second insulating substrate 30, fixed on top of first insulating substrate 29 and electrodes 31 and 32 by the use of hot melt adhesive (not shown). Substrate 30 is about 250 microns thick, made of polyester, and includes window 35 which exposes substantially equal surface areas of electrodes 31 and 32. Substrate 30 also has cutout portion 34 at one end to allow an electrical connection between the electrodes and a power source (not shown) and a current measuring meter (not shown).

Immunosensor 28 also has a polyester mesh 36. Polyester mesh 36 may be any porous substrate that has sufficient porosity to allow passage of a whole blood sample. Examples of porous substrates that may be used include meshes, films, soluble polymers, and membranes. Polyester mesh 36 is impregnated with the ED reagent (described above) by dispensing about 5 $\mu$l of the ED reagent directly onto mesh 36. Mesh 36 is then dried by heating at about 50° C. for about 15 minutes. After the reagent has dried, mesh 36 is affixed above window 35 in second insulating substrate 30 as shown in FIG. 7.

About 6 µl of EA reagent 37 (described above) is dispensed directly onto second insulating substrate 30 as shown in FIG. 7. Third insulating substrate 38 is placed over second insulating substrate 30. Third insulating substrate 38 is a thin insulating substrate which preferably has adhesive material on each side to hold it in place. Third insulating substrate 38 includes cutout portion 41. Fourth insulating substrate 39 (not shown in FIG. 6) is placed over third insulating substrate 38, such that a capillary space is formed within cutout portion 41 of third insulating substrate 38 which allows capillary flow from EA reagent 37 to polyester mesh 36 (which is impregnated with ED reagent). Fourth insulating substrate 39 is about 250 microns thick, made of polyester, and includes sample window 40 (not shown in FIG. 6) which exposes EA reagent 37, and vent hole 42 (not shown in FIG. 6).

Immunosensor 28 may be used to determine the concentration of an analyte in a whole blood sample by the following method. Whole blood sample 43 (about 20 µl) is applied to sample window 40 of immunosensor 28. A mixture of EA reagent 37 and blood sample 43 is formed, which is drawn to polyester mesh 36 by capillary action caused by cutout portion 41 and vent 42. The ED reagent, impregnated in mesh 36, then becomes part of the mixture. The mixture of EA reagent 37, ED reagent, and blood sample 42 then settles on electrodes 31 and 32 through window 35 of second insulating substrate 30. After an incubation period of about 20 minutes, a potential difference of 450 mV is applied between electrodes 31 and 32 (electrically connected to a power source and a current measuring meter). The current generated is measured for about 5 seconds. The amount of current measured 3 seconds after application of the potential difference is then compared to a calibration curve and analyte concentration in the whole blood sample is determined.

Example 3 theophylline assay using a dry-chemistry immunosensor

Another example of a dry chemistry immunosensor that can be used to practice the present invention will now be described. Immunosensor 44 shown in FIGS. 8 & 9 includes first insulating substrate 45, working electrode 47, counter electrode 48, insulator material 49, second insulating substrate 46, cutout portion 50, and window 51, which are all similar in composition and function to first insulating substrate 29, working electrode 31, counter electrode 32, insulator material 33, second insulating substrate 30, cutout portion 34, and window 35 described above in FIGS. 6 & 7. (A two-electrode electrocell, utilizing working and reference electrodes, and a three-electrode electrocell are also possible, as described above for electrocell 19 and immunosensor 28.)

Figure 8:
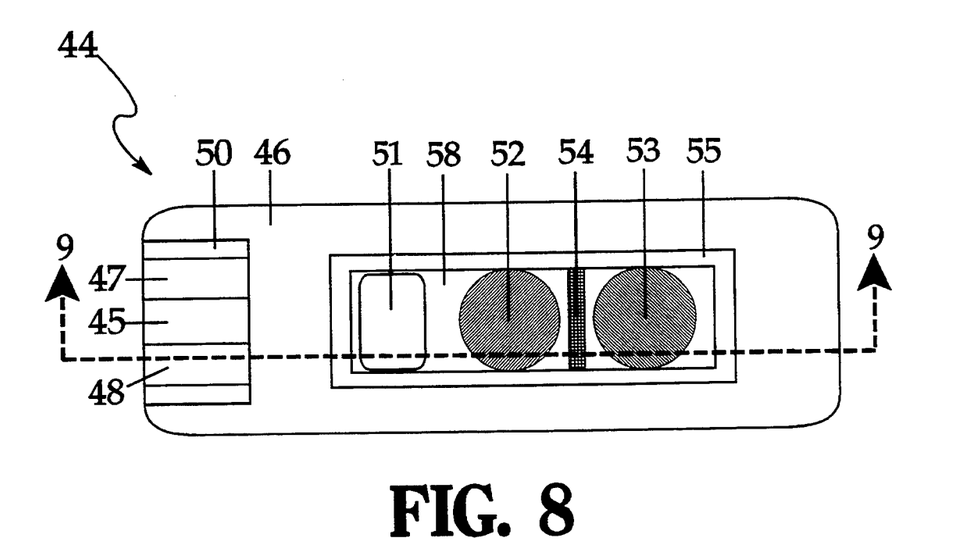
FIG. 8 is a schematic top view of an embodiment of an immunesensor of the present invention, excluding the fourth insulating substrate.
Figure 9:
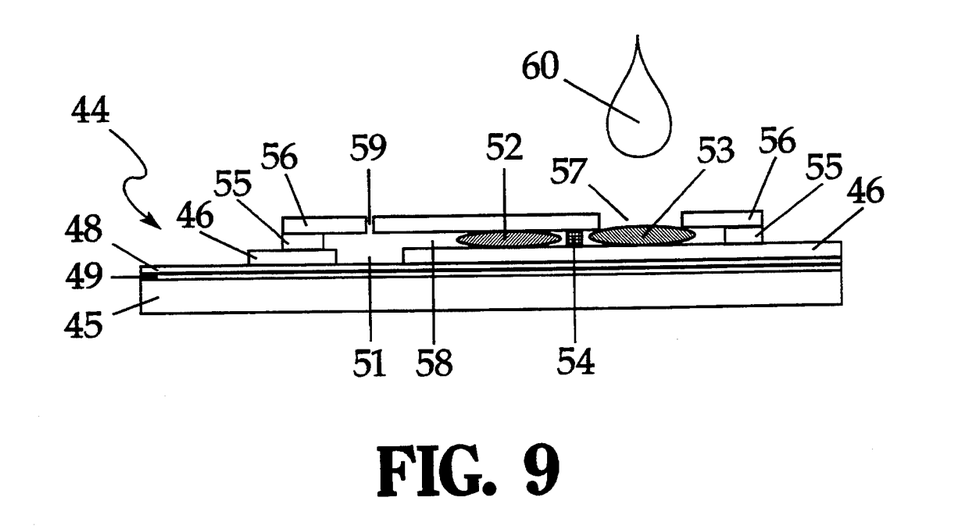
FIG. 9 is a schematic cross-sectional view of FIG. 8 taken along line 9—9 of FIG. 8, including the fourth insulating substrate.

About 5 µL of ED reagent 52 and 6 µL of EA reagent 53 are dispensed directly onto second insulating substrate 46 as shown in FIGS. 8 & 9. ED reagent 52 and EA reagent 53 are made as described above, dispensed onto second insulating substrate 46, then dried by heating at about 50° C. for about 15 minutes. Second insulating substrate 46 also has polymer 54, placed between ED reagent 52 and EA reagent 53. Polymer 54 can be any water-soluble polymer, such as polyvinyl pyridine, polyvinyl pyrrolidone, or polyvinyl imidazole, and preferably should be non-electroactive and non-reactive.

Third insulating substrate 55 is placed over second insulating substrate 46. Third insulating substrate 55 is a thin insulating substrate which preferably has adhesive material on each side to hold it in place. Third insulating substrate 55 includes cutout portion 58. Fourth insulating substrate 56 (not shown in FIG. 8) is placed over third insulating substrate 55, such that capillary space is formed within cutout portion 58 of third insulating substrate 55 which allows capillary flow from EA reagent 53 to ED reagent 52. Fourth insulating substrate 56 is about 250 microns thick, made of polyester, and includes sample window 57 (not shown in FIG. 8) which exposes EA reagent 53, and vent hole 59 (not shown in FIG. 8).

Immunosensor 44 may be used to determine the concentration of an analyte in a whole blood sample by the following method. Whole blood sample 60 (about 20 µl) is applied to sample window 57 of immunosensor 44. A mixture of EA reagent 53 and blood sample 60 is formed. Polymer 54 allows whole blood sample 60 and EA reagent 53 to mix and react for a predetermined period of time, during which time polymer 54 is dissolved. After polymer 54 has dissolved, the solution of whole blood sample 60, EA reagent 53 and polymer 54 then flows to ED reagent 52 to complete mixing the immunoassay reaction components. The EA reagent 53, ED reagent 52, polymer 54, and blood sample 60 mixture is then drawn by capillary action (caused by cutout portion 58 and vent hole 59) to window 51 and settles on electrodes 47 and 48. After an incubation period of about 20 minutes, a potential difference of 450 mV is applied between electrodes 47 and 48 (electrically connected to a power source and a current measuring meter). The current generated is measured for about 5 seconds. The amount of current measured 3 seconds after application of the potential difference is then compared to a calibration curve and analyte concentration in the whole blood sample is determined.

The meter and power source described above for use with electrocell 19 and immunosensors 28 and 44 will normally be adapted to apply an algorithm to the current measurement, whereby the analyte level is provided and visually displayed. Improvements in such a power source and meter are the subject of commonly assigned U.S. Pat. No. 4,963,814—"Regulated Bifurcated Power Supply" (Parks et al., issued Oct. 16, 1990), U.S. Pat. No. 4,999,632—"Analog to Digital Conversion with Noise Reduction" (Parks, issued Mar. 12, 1991), U.S. Pat. No. 4,999,582—"Biosensor Electrode Excitation Circuit" (Parks et al., issued Mar. 12, 1991), and U.S. Pat. No. 5,243,516—"Biosensing instrument and Method" (White, issued Sep. 7, 1993), the disclosures of which are hereby incorporated by reference.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

What is claimed is:

1. A diagnostic kit useful for an immunoassay of an analyte in a fluid sample, wherein the immunoassay utilizes an electrochemical measurement, the kit comprising:

(a) an enzyme donor reagent, which includes 1) an enzyme-donor polypeptide conjugate, and
2) a labeled substrate, wherein the labeled substrate is 4(1,4,7,10-tetraoxadecyl)-1-naphthyl-$\beta$-D-galactopyranoside or 4-methoxyl-1-naphthyl-$\beta$-D-galactopyranoside; and (b) an enzyme acceptor reagent, which includes
1) an enzyme-acceptor polypeptide capable of combining with the enzyme-donor polypeptide conjugate to form an active enzyme complex capable of catalyzing the cleavage of the substrate label from the substrate, and
2) a first antibody capable of immunologically, competitively binding to the analyte and the enzyme-donor polypeptide conjugate and hindering formation of the active enzyme complex when bound to the enzyme-donor polypeptide conjugate.

2. The diagnostic kit of claim 1, wherein the enzyme donor reagent and the enzyme acceptor reagent further include a buffer that is substantially non-electroactive at the potential used for the electrochemical measurement.

3. The diagnostic kit of claim 2, wherein the enzyme donor reagent further includes an amount of added peptides, protein fragments, or proteins sufficient to reduce hydrolysis of the enzyme-donor polypeptide conjugate from proteases in the fluid sample.

4. The diagnostic kit of claim 3, wherein the enzyme acceptor reagent further includes a second antibody capable of immunologically binding to the first antibody, thereby further hindering formation of the active enzyme complex when the first antibody is bound to the enzyme-donor polypeptide conjugate.

5. The diagnostic kit of claim 4, wherein the enzyme acceptor reagent further includes an amount of the analyte sufficient to ensure that changes in concentration of the analyte in the fluid sample are substantially linearly related to changes in the current measured by the electrochemical measurement.

6. The diagnostic kit of claim 3, wherein the analyte is theophylline.

7. The diagnostic kit of claim 4, wherein the analyte is theophylline, the added peptides, protein fragments, or proteins are fragmented bovine serum albumin, and the second antibody is heat-inactivated goat anti-mouse serum.

8. The diagnostic kit of claim 1, further comprising:
(c) an electrochemical cell, which includes
1) a first insulating substrate;
2) working and counter electrodes affixed to the first insulating substrate; and
3) a second insulating substrate, which overlays the working and counter electrodes, has a window for exposing a portion of the working and counter electrodes, and has a cut out portion at one end to allow contact between the electrodes and a meter and a power source.

9. The diagnostic kit of claim 8, wherein the working and counter electrodes are palladium, platinum, gold, silver, titanium, copper, or carbon.

10. The diagnostic kit of claim 9, wherein the working and counter electrodes are made of the same material and are substantially the same size.

11. The diagnostic kit of claim 10, wherein the enzyme donor reagent and the enzyme acceptor reagent further include a buffer that is substantially non-electroactive at the potential used for the electrochemical measurement.

12. The diagnostic kit of claim 11, wherein the enzyme donor reagent further includes an amount of added peptides, protein fragments, or proteins sufficient to reduce hydrolysis of the enzyme-donor polypeptide conjugate from proteases in the fluid sample.

13. The diagnostic kit of claim 12, wherein the enzyme acceptor reagent further includes a second antibody capable of immunologically binding to the first antibody, thereby further hindering formation of the active enzyme complex when the first antibody is bound to the enzyme-donor polypeptide conjugate.

14. The diagnostic kit of claim 13, wherein the enzyme acceptor reagent further includes an amount of the analyte sufficient to ensure that changes in concentration of the analyte in the fluid sample are substantially linearly related to changes in the current measured by the electrochemical measurement.

15. The diagnostic kit of claim 14, further comprising:
(d) the power source in electrical connection with the working and counter electrodes and capable of supplying an electrical potential difference between the working and counter electrodes sufficient to cause electrooxidation of the reduced form of the label at the surface of the working electrode; and
(e) the meter in electrical connection with the working and counter electrodes and capable of measuring the current produced by the oxidation of the reduced form of the label at the working electrode surface.

16. The diagnostic kit of claim 14, wherein the analyte is theophylline.

17. The diagnostic kit of claim 15, wherein the analyte is theophylline, the added peptides, protein fragments, or proteins are fragmented bovine serum albumin, and the second antibody is heat-inactivated goat anti-mouse serum.

18. An immunoassay method for determining the concentration of an analyte in a fluid sample, wherein the immunoassay utilizes an electrochemical measurement, the method comprising:
(a) preparing a mixture which includes
1) the fluid sample,
2) an enzyme acceptor polypeptide,
3) a labeled substrate, wherein the labeled substrate is 4-(1,4,7,10-tetraoxadecyl)-1-naphthyl-$\beta$-D-galactopyranoside or 4-methoxy-1-naphthyl-$\beta$-D-galactopyranoside,
4) an enzyme-donor polypeptide conjugate, capable of combining with the enzyme acceptor polypeptide to form an active enzyme complex capable of catalyzing the cleavage of the label from the substrate, the label being electroactive at the potential used for the electrochemical measurement when cleaved from the substrate, and
5) a first antibody, capable of immunologically, competitively binding to the analyte and the enzyme-donor polypeptide conjugate and hindering formation of the active enzyme complex when bound to the enzyme-donor polypeptide conjugate;
(b) applying the mixture to an electrochemical cell having working and reference electrodes;
(c) applying, after incubation of the mixture, a potential difference between the working and reference electrodes sufficient to oxidize the label that has been cleaved from the substrate, thereby generating a current; and (d) measuring the current and correlating the current to analyte concentration.

19. The immunoassay method of claim 18, wherein the mixture further includes a buffer that is substantially non-electroactive at the potential used for the electrochemical measurement.

20. The immunoassay method of claim 19, wherein the mixture further includes an amount of added peptides, protein fragments, or proteins sufficient to reduce hydrolysis of the enzyme-donor polypeptide conjugate from proteases in the mixture.

21. The immunoassay method of claim 20, wherein the mixture further includes a second antibody capable of immunologically binding to the first antibody, thereby further hindering formation of the active enzyme complex when the first antibody is bound to the enzyme-donor polypeptide conjugate.

22. The immunoassay method of claim 21, wherein the mixture further includes an amount of the analyte sufficient to ensure that changes in concentration of the analyte in the fluid sample are substantially linearly related to changes in the current measured by the electrochemical measurement.

23. The immunoassay method of claim 21, wherein the electrochemical cell comprises:
  (a) a first insulating substrate;
  (b) working and reference electrodes affixed to the first insulating substrate; and
  (c) a second insulating substrate, which overlays the working and reference electrodes, has a window for exposing a portion of the working and reference electrodes, and has a cut out portion at one end to allow contact between the electrodes and a current measuring meter and a power source.

24. The immunoassay method of claim 23, wherein the analyte is theophylline.

25. The immunoassay method of claim 24, wherein the added peptides, protein fragments, or proteins are fragmented bovine serum albumin, and the second antibody is heat-inactivated goat anti-mouse serum.

26. An immunoassay method for determining the presence of an analyte in a fluid sample, wherein the immunoassay utilizes an electrochemical measurement, the method comprising:
  (a) preparing a mixture which includes
    1) the fluid sample,
    2) an enzyme acceptor polypeptide,
    3) a labeled substrate, wherein the labeled substrate is 4-(1,4,7,10-tetraoxadecyl)-1-naphthyl-$\beta$-D-galactopyranoside or 4-methoxy-1-naphthyl-$\beta$-D-galactopyranoside,
    4) an enzyme-donor polypeptide conjugate, capable of combining with the enzyme acceptor polypeptide to form an active enzyme complex capable of catalyzing the cleavage of the label from the substrate, the label being electroactive at the potential used for the electrochemical measurement when cleaved from the substrate, and
    5) a first antibody, capable of immunologically, competitively binding to the analyte and the enzyme-donor polypeptide conjugate and hindering formation of the active enzyme complex when bound to the enzyme-donor polypeptide conjugate;
  (b) applying the mixture to an electrochemical cell having working and counter electrodes;
  (c) applying a potential difference between the working and counter electrodes sufficient to oxidize the label that has been cleaved from the substrate, thereby generating a current; and
  (d) measuring the current and correlating the current to the presence of the analyte.

27. The immunoassay method of claim 26, wherein the mixture further includes a buffer that is substantially non-electroactive at the potential used for the electrochemical measurement.

28. The immunoassay method of claim 27, wherein the mixture further includes an amount of added peptides, protein fragments, or proteins sufficient to reduce hydrolysis of the enzyme-donor polypeptide conjugate from proteases in the mixture.

29. The immunoassay method of claim 28, wherein the mixture further includes a second antibody capable of immunologically binding to the first antibody, thereby further hindering formation of the active enzyme complex when the first antibody is bound to the enzyme-donor polypeptide conjugate.

30. The immunoassay method of claim 29, wherein the electrochemical cell comprises:
  (a) a first insulating substrate;
  (b) working and counter electrodes affixed to the first insulating substrate; and
  (c) a second insulating substrate, which overlays the working and counter electrodes, has a window for exposing a portion of the working and counter electrodes, and has a cut out portion at one end to allow contact between the electrodes and a current measuring meter and a power source.

31. The immunoassay method of claim 30, wherein the analyte is theophylline.

32. The immunoassay method of claim 31, wherein the added peptides, protein fragments, or proteins are fragmented bovine serum albumin, and the second antibody is heat-inactivated goat anti-mouse serum.

33. An immunosensor useful for an electrochemical immunoassay of an analyte in an fluid sample, comprising:
  (a) a first insulating substrate;
  (b) working and counter electrodes affixed to the first insulating substrate;
  (c) a second insulating substrate, which overlays the working and counter electrodes, has a window for exposing substantially equal surface areas of the working and counter electrodes, and has a cut out portion at one end to allow contact between the electrodes and a meter and a power source;
  (d) a porous substrate, which is impregnated with an enzyme donor reagent, overlays the window, and is spatially displaced from the working and counter electrodes, the enzyme donor reagent including
    1) an enzyme-donor polypeptide conjugate, and
    2) a labeled substrate, the label being substantially non-electroactive at the potential used for the electrochemical measurement when attached to the substrate, and being electroactive at the potential used for electrochemical measurement when cleaved from the substrate;
  (e) an enzyme acceptor reagent, which is placed on the second insulating substrate, the enzyme acceptor reagent including
    1) an enzyme-acceptor polypeptide capable of combining with the enzyme-donor polypeptide conjugate to form an active enzyme complex capable of catalyzing the cleavage of the substrate label from the substrate, and 2) a first antibody capable of immunologically, competitively binding to the analyte and the enzyme-donor polypeptide conjugate and hindering formation of the active enzyme complex when bound to the enzyme-donor polypeptide conjugate;

(f) a third insulating substrate, which overlays the second insulating substrate and has a cutout portion for exposing the enzyme-donor reagent, the enzyme-acceptor reagent, and the window in the second insulating substrate; and (g) a fourth insulating substrate, which overlays the third insulating substrate such that a capillary space is formed within the cutout portion of the third insulating substrate, has a window for exposing a portion of the enzyme acceptor reagent, and has a vent hole.

34. The immunosensor of claim 30, wherein the working and counter electrodes are palladium, platinum, gold, silver, titanium, copper, or carbon.

35. The immunosensor of claim 34, wherein the working and counter electrodes are made of the same material and are substantially the same size.

36. The immunosensor of claim 34, wherein the porous substrate is a mesh, a membrane, or a porous film.

37. The immunosensor of claim 35, wherein the porous substrate is a polyester mesh.

38. The immunosensor of claim 37, further comprising:

(h) the power source in electrical connection with the working and counter electrodes and capable of supplying an electrical potential difference between the working and counter electrodes sufficient to cause electrooxidation of the reduced form of the label at the surface of the working electrode; and (i) the meter in electrical connection with the working and counter electrodes and capable of measuring the current produced by the oxidation of the reduced form of the label at the working electrode surface.

39. The immunosensor of claim 38, wherein the labeled substrate is 4-(1,4,7,10-tetraoxadecyl)-1-naphthyl-$\beta$-D-galactopyranoside or 4-methoxy-1-naphthyl-$\beta$-D-galactopyranoside.

40. The immunosensor of claim 39, wherein the analyte is theophylline.

41. The immunosensor of claim 39, wherein the enzyme donor reagent further includes an amount of added peptides, protein fragments, or proteins sufficient to reduce hydrolysis of the enzyme-donor polypeptide conjugate from proteases in the fluid sample.

42. The immunosensor of claim 41, wherein the enzyme acceptor reagent further includes a second antibody capable of immunologically binding to the first antibody, thereby further hindering formation of the active enzyme complex when the first antibody is bound to the enzyme-donor polypeptide conjugate.

43. The immunosensor of claim 42, wherein the enzyme acceptor reagent further includes an amount of the analyte sufficient to ensure that changes in concentration of the analyte in the fluid sample are substantially linearly related to changes in the current measured by the electrochemical measurement.

44. The immunosensor of claim 43, wherein the analyte is theophylline, the added peptides, protein fragments, or proteins are fragmented bovine serum albumin, and the second antibody is heat-inactivated goat anti-mouse serum.

45. An immunosensor useful for an electrochemical immunoassay of an analyte in a fluid sample, comprising:

(a) a first insulating substrate;

(b) working and reference electrodes affixed to the first insulating substrate;

(c) a second insulating substrate, which overlays the working and reference electrodes, has a window for exposing substantially equal surface areas of the working and reference electrodes, and has a cut out portion at one end to allow contact between the electrodes and a meter and a power source;

(d) an enzyme donor reagent, which is placed on the second insulating substrate, the enzyme donor reagent including
   1) an enzyme-donor polypeptide conjugate, and
   2) a labeled substrate, the label being substantially non-electroactive at the potential used for the electrochemical measurement when attached to the substrate, and being electroactive at the potential used for electrochemical measurement when cleaved from the substrate;

(e) an enzyme acceptor reagent, which is placed on the second insulating substrate, the enzyme acceptor reagent including
   1) an enzyme-acceptor polypeptide capable of combining with the enzyme-donor polypeptide conjugate to form an active enzyme complex capable of catalyzing the cleavage of the substrate label from the substrate, and
   2) a first antibody capable of immunologically, competitively binding to the analyte and the enzyme-donor polypeptide conjugate and hindering formation of the active enzyme complex when bound to the enzyme-donor polypeptide conjugate;

(f) a polymer, which is placed on the second insulating substrate between the enzyme acceptor reagent and the enzyme donor reagent;

(g) a third insulating substrate, which overlays the second insulating substrate and has a cutout portion for exposing the enzyme-donor reagent, the enzyme-acceptor reagent, the polymer, and the window in the second insulating substrate; and (h) a fourth insulating substrate, which overlays the third insulating substrate such that a capillary space is formed within the cutout portion of the third insulating substrate, has a window for exposing a portion of the enzyme acceptor reagent, and has a vent hole.

46. The immunosensor of claim 45, wherein the working and reference electrodes are palladium, platinum, gold, silver, titanium, copper, or carbon.

47. The immunosensor of claim 46, wherein the reference electrode is a silver/silver chloride reference electrode.

48. The immunosensor of claim 47, further comprising:

(i) the power source in electrical connection with the working and reference electrodes and capable of supplying an electrical potential difference between the working and reference electrodes sufficient to cause electrooxidation of the reduced form of the label at the surface of the working electrode; and (j) the meter in electrical connection with the working and reference electrodes and capable of measuring the current produced by the oxidation of the reduced form of the label at the working electrode surface.

49. The immunosensor of claim 48, wherein the labeled substrate is 4-(1,4,7,10-tetraoxadecyl)-1-naphthyl-β-D-galactopyranoside or 4-methoxy-1-naphthyl-β-D-galactopyranoside.

50. The immunosensor of claim 49, wherein the analyte is theophylline.

51. The immunosensor of claim 50, wherein the enzyme donor reagent further includes an amount of added peptides, protein fragments, or proteins sufficient to reduce hydrolysis of the enzyme-donor polypeptide conjugate from proteases in the fluid sample.

52. The immunosensor of claim 51, wherein the enzyme acceptor reagent further includes a second antibody capable of immunologically binding to the first antibody, thereby further hindering formation of the active enzyme complex when the first antibody is bound to the enzyme-donor polypeptide conjugate.

53. The immunosensor of claim 52, wherein the enzyme acceptor reagent further includes an amount of the analyte sufficient to ensure that changes in concentration of the analyte in the fluid sample are substantially linearly related to changes in the current measured by the electrochemical measurement.

54. The immunosensor of claim 53, wherein the analyte is theophylline, the added peptides, protein fragments, or proteins are fragmented bovine serum albumin, and the second antibody is heat-inactivated goat anti-mouse serum.

* * * * *

UNITED STATES PATENT AND TRADEMARK OFFICE
CERTIFICATE OF CORRECTION

PATENT NO.  : 5,427,912
DATED       : June 27, 1995
INVENTOR(S) : Mary E. Brown, et. al.

It is certified that error appears in the above-indentified patent and that said Letters Patent is hereby corrected as shown below:

Title page, item [75], inventor:  add John G.R. Hurrell, Carmel, Indiana. Hans-Hoachim Guder, Grunstadt, Federal Republic of Germany--.

Signed and Sealed this

Second Day of January, 1996

Attest:

BRUCE LEHMAN

Attesting Officer

Commissioner of Patents and Trademarks